United States Patent [19]
Abrams

[11] Patent Number: 5,098,384
[45] Date of Patent: Mar. 24, 1992

[54] PRESSURE-COMPENSATED FLUID ADMINISTERING APPARATUS

[76] Inventor: Lawrence M. Abrams, 133 Huguenot Ave., Englewood, N.J. 07631

[21] Appl. No.: 644,895

[22] Filed: Jan. 23, 1991

[51] Int. Cl.$^5$ ............................................. A61M 1/00
[52] U.S. Cl. ..................................... 604/118; 73/747
[58] Field of Search ................... 604/118; 73/747, 749, 73/750

[56] References Cited

U.S. PATENT DOCUMENTS

| | | | |
|---|---|---|---|
| 2,105,127 | 1/1938 | Petroe | 73/747 |
| 2,600,324 | 6/1952 | Rappaport | 73/749 |
| 2,615,940 | 10/1952 | Williams | 73/749 |
| 3,611,811 | 10/1971 | Lissau | 73/747 |
| 4,769,001 | 9/1988 | Prince | 604/118 |
| 4,820,265 | 4/1989 | DeSatmick et al. | 604/118 |
| 4,902,277 | 2/1990 | Mathers et al. | 604/154 |

*Primary Examiner*—Paul J. Hirsch
*Attorney, Agent, or Firm*—Herbert M. Shapiro

[57] ABSTRACT

Patient pressure monitoring systems require constant monitoring and adjustment by patient care specialists because of erroneous indications of changes in blood pressure readings which occur is such systems. The changes are due to errors produced by the sensing system caused by patient movement with respect to the pressure sensor. Such erroneous changes are eliminated by the addition of a second fluid path which is maintained at atmospheric pressure and controllably is connected to the prime fluid path to normalize any change in pressure in the prime path due to changes in relative positions of the sensor and the patient.

11 Claims, 2 Drawing Sheets

PRESSURE-COMPENSATED FLUID ADMINISTERING APPARATUS

FIELD OF THE INVENTION

This invention relates to pressure monitoring systems and, more particularly, to such systems which include means for normalizing unwanted pressure variations due to instrumentation movement.

BACKGROUND OF THE INVENTION

Pressure monitoring systems for patient care are most frequently used in fluid flush systems. A typical flush system includes a pressurized bag in which the pressure is maintained at approximately 300 mm Hg or 400 cms of water. The purpose of the bag is to provide a source of fluid to flush the line to the patient, either to fill the line with fluid or to flush blood back to the patient after blood fills the system during blood withdrawal. It is also used as a sorce of continuous flush to keep blood from forming clots over the end of an indwelling catheter connecting the tubing to the patients vascular system. The pressure in the bag must be greater than the patients blood pressure (about 100 mm Hg.) so that it can overcome the back pressure during intermittent flush. Continuous flush occurs via a restrictor mechanism as is well known. Whether the system is used in the continuous or the intermittent mode, the system is in series with the pressurized bag and the downstream components of the system. For continuous flush, the system consists of a restrictor designed to allow about 3 cc/hour of fluid to flow across an upstream-downstream pressure gradient of 200 mm Hg (300 minus the back pressure of a nominal 100). A restrictor this tight adds nearly no additional pressure to the system, and what little it does produce is a continuous bias accounted for during the process of zeroing the system as described more fully hereinafter.

The intermittent flush is simply a bypass valve that allows the full upstream pressure to bypass the restrictor and produce a rapid flush of the system. Typically, such valves consist of a mechanism which, when pressed or sqeezed, allows a valving mechanism to open. Thus, the fail-safe condition of the valve is a no-pass condition, a safety feature necessary to protect the downstream environment (patient) from potentialy harmfull pressures and flows.

Such a system also includes a transducer. The transducer is traditionally a "gage" type of pressure sensing device, meaning that it senses system pressure and uses atmospheric pressure as it's reference. This type of transducer has been used because it requires only one surface of the transducer to be exposed to the system environment. The other side of the transducer, in addition to being exposed to atmospheric pressure, interfaces with the electronic and mechanical components of the transducer. Because of the technical nature of the transducer, little emphasis has been placed on true differential sensing. Instead, there has developed a nearly universal acceptance of the use of unchanging atmospheric pressure as a default.

The transducer may be placed upstream or downstream from the flush device. If it is downstream, the transducer chamber has two ports. Fluid enters one port as it travels from the flush device to the transducer. It then travels through the transducer, purging it of air, and exits the second port, toward the patient. If the transducer is located upstream from the flush device, it is "dead ended" on one arm of a "T" arrangement, with the fluid from the reservoir bag entering the stem of the "T" and then either passing upstream to the transducer or downstream to the patient. The second port of the transducer is then opened only to allow air to purge the system during priming. Then it is closed.

At various locations in the system, there are located stopcocks (valves) which serve the function of either isolating regions or of venting ports when appropriate.

The configuration of the system is such that a first column of tubing extends from the transducer (or flush device) to the patient. As a result, there is a continuous column of fluid extending from the transducer to the patients' vascular system and from there to his heart.

The reservoir bag is pressurized to 300 mm Hg, a nominal setting. While the system is set for this pressure, it's function is not guaranteed even if the pressure is maintained at a constant level. This is so because the flush system is most dependent on the setting as it depends on the upstream pressure to provide the driving force necessary to maintain the 3 cc/hour flow through the restrictor, assuming the downstream pressure to be a mean of 100 mm Hg.

But, in practice the pressure is not maintained at a constant value because the means for maintaining the upstream pressure—an inflated bag— is an inconstant source, requiring frequent reinflations, and the pressure gages are not sufficiently precise. Added consideration are that the accuracy of the resrictors is highly variable and the downstream pressures are rarely at the designated target value because blood pressure varies widely. Frequently, flush systems are used to measure the venous system pressures, normally at mean pressures of 10-20 mm Hg or less where imprecisions of such systems lead to excessive continuous flush.

The transducer for such a system is available in a variety of types. Specifically, pressure is sensed either by electrical or mechanical means. Electrical transducers also are of a variety of types including strain gages, silcon chip, conductance, inductance, reluctance, etc. Mechanical types include diaphragm-needle gages, fluid columns, Mercury manometers, etc. The transducer is always "differential" in that it measures the target pressure relative to a second pressure. If the second pressure is atmospheric pressure, it is termed a "gage". If the second pressure is a vacuum, it is an absolute pressure. If the second pressure is a pressure within a controlled chamber, the transducer is called "differential".

The transducer may or may not be able to measure liquids as well as gases or it may be able to accept liquids on only one side of it's pressure sensitive member, allowing only gas on the other side of the member. It is therefor either dry/dry, wet/dry or wet/wet.

In most medical pressure measuring situations, either dry/dry or wet/dry instrumentation is used, whether it is electrical or mechanical. Wet/wet capability imposes more complex issues. In electrical transducers, one surface of the pressure sensing element can face the environment to be measured, but the backside of the sensing element contains sensitive electronic components. Making the backside safe for exposure to liquids is a more complex and expensive procedure. Additionally, for disposable systems, or for nondisposable systems which must be cleaned, constructing an isolating chamber for the backside imposes cost considerations that render a true differential wet/wet type of transducer impractical. Purely mechanical differential gages of transducers suffer much the same problems. In any case, the transducer has to be calibrated to establish a reference or "zero" value. Zeroing a fluid filled transducer traditionally means isolating the chamber on the sensing side of the transducer and filling the chamber with fluid (if the system is to measure fluid pressure) and often opening the transducer to atmospheric pressure. The electrical or mechanical signal produced by the pressure sensing member under these conditions is taken as "zero". When the chamber is then close to the atmosphere and opened to the measuring pressure, the system has nulled all the factors except the ones desired to be measured, and reads the pressure relative to atmospheric pressure.

If the the system to be measured is distant from the transducer, and contains fluid, there must be a continuous fluid path or pipe connecting to the system to be measured. Since the fluid has a density greater than air, which is the reference medium generating the reference pressure, the vertical height of the fluid column between the transducer and the site of measurement must be considered. The pressure measurement at the transducer is the pressure at the site of importance plus or minus the pressure generated by the fluid column that exists between the transducer and the site of measurement.

From a practical point of view, this system causes some problems. In medical applications, a fluid filled medium that must stay stagnant yet be directly coupled to a the patient's circulatory system imposes considerable risk of contamination. For this reason, regulatory authorities impose strict rules to ensure integrity of the system. One of these rules is that the system must be "closed". The zeroing procedure described above, while allowed because it is necessary, by definition violates the closed integrity of the system. Additionally, opening the system, and then flushing the chamber to flush out any air which may have collected, causes fluid to spill out of the port, most often onto the floor or onto the patients bed. Such practices certainly are undesirable at best.

In medical applications, the blood pressure that is taken as standard is the pressure at the central aorta at the point of exit from the heart. Venous pressure is taken as Central Venous Pressure (CVP), which is the pressure that exists in the right Atrium of the heart. Other physiological pressures are often taken at specific locations within the body, e.g. the brain, the pulmanary artery, the chest, the esophagus, the stomach, etc.

Two procedures must be followed to ensure that the transducer in each of these procedures, reads correctly. First, the zeroing procedure, described above, must be undertaken. This causes the transducer to read atmospheric pressure as zero. Second, a levelling procedure must be undertaken to ensure that the pressure read by the transducer corresponds exactly with the pressure at the site being measured, by physically eliminating any vertial columns. Simply speaking, this means that some method is employed to move the point of the transducer that was opened to air during the zeroing procedure to a vertical level exactly the same as the vertical height of the target site.

The methods employed for this second procedure are somewhat crude and basic. Most commonly, the practitioner "eyeballs" the system to a point that "looks right". If available, an actual levelling device is used. A somewhat more sophisticated approach is to take the tubing which goes to the patient and hold an exposed and open end of it at a point immediately adjacent to a point on the body closest to the target site. Such an approach, of course, exposes the system to contamination. Once the tubing is in the proper location, one may physically adjust the vertical height of the transducer until it reads zero, or one may "tell" the instrument that the pressure it then reads is to be called "zero" In any case, should the patients vertical height change or should the vertical position of the transducer change, this procedure must be repeated. In practice, this is one of the greatest sources of inaccuracy.

The problem with this arrangement is that, in normal operation, changes in the vertical position of the patient with respect to that of the pressure sensor appears to the sensor as a change in blood pressure. A mere four inch change in vertical height can signal a 10% change in blood pressure for a normal patient with a blood pressure of 100 centimetes (CMS) of water. For neonatal patients, where blood pressure normally is 40 to 50 CMS of water, that change in vertical height can signal a dramatic change in blood pressure calling for heroic efforts on the part of attending health care specialists which may be counterproductive or even fatal.

BRIEF DESCRIPTIONS OF EMBODIMENTS OF THIS INVENTION

In accordance with the principles of this invention, a pressure sensor is connected so that any change in the vertical position of a patient relative to that of the sensor is normalized so that the instrumentation does not register a change in pressure when a change in vertical postion occurs. The normalization is produced by exposing the backside surface of the sensor to a second column of fluid. One end of the second column is controllably connected to the first column on the patient side of the sensor (down stream). The other end of the second column is exposed to atmospheric pressure and is connected, illustratively, to the patients chest wall. The first column is the vertical height from the patient's side of the transducer to the insertion point in the vessel and then to the origen of the fluid, i.e., the aortic valve of the heart. Thus, the heights of the two columns are always equal to one another and any change in the vertical position of a patient with respect to that of the sensor appears as an equal change in the height of the fluid in both columns. The monitoring system does not indicate any false blood pressure readings due to a change in vertical position.

DETAILED DESCRIPTION OF ILLUSTRATIVE EMBODIMENTS OF THIS INVENTION

Figure 1:
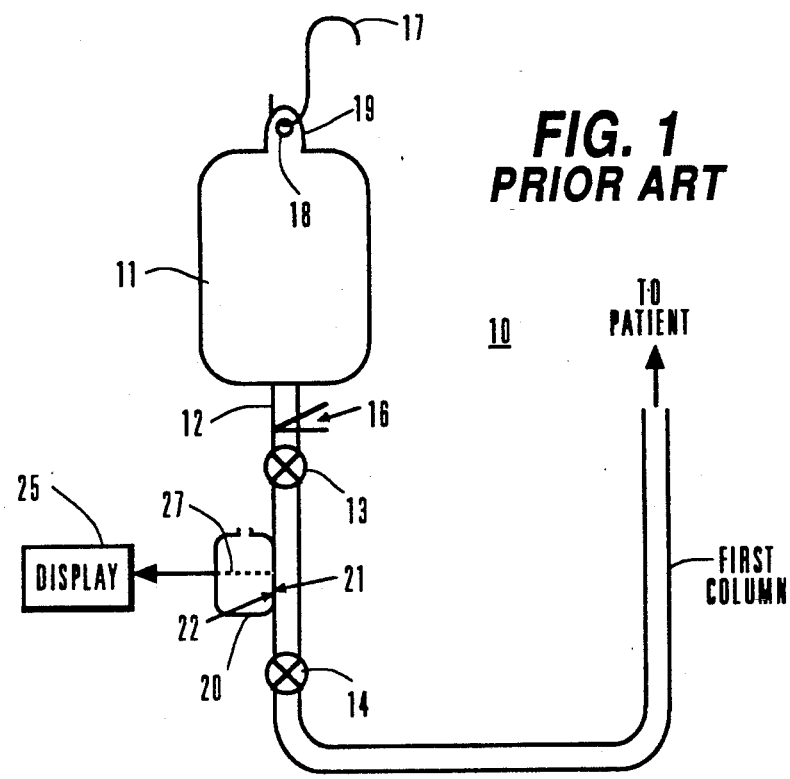
FIG. 1 is a schematic illustration of a prior art patient fluid delivery system in common use.

FIG. 1 shows a prior art pressure monitoring system 10 for patient end use. The system includes a fluid container 11 which is a reservoir for fluid. The fluid container normally is sealed and pressurized to 300 mm of Mercury (420 CMS of water). The system also includes a tube 12 which extends from the reservoir and terminates at it's distal end in a hypodermic needle for connection to the vascular system of a patient. The tube includes several stop cocks 13 and 14 for interupting fluid flow and at least one fluid control valve 16 for regulating fluid flow in the system. The system also includes a pressure sensor 20 one surface (21) of which is exposed to the fluid. The second surface (22) of the sensor is exposed to air as shown.

The pressure sensor is connected to an electronic display 25. Display 25 is calibrated with respect to a reference pressure by flushing the system with fluid and by measuring the pressure of the fluid. The backside surface, 22, of the sensor is at atmospheric pressure and so the reference pressure turns out to be the reference pressure under the conditions specified. In fact, the reference pressure is the pressure at the vertical distance of the patient's heart with respect to the sensor. If that vertical distance, measured, say, at broken horizontal line 27, later changes, the calibration is no longer valid and false readings result. Frequent changes in the patients position do occur and such changes do lead to frequent changes in the blood pressure readings. This, in turn, leads to a requirement of frequent monitoring and retraining by trained health care specialists.

Figure 2:
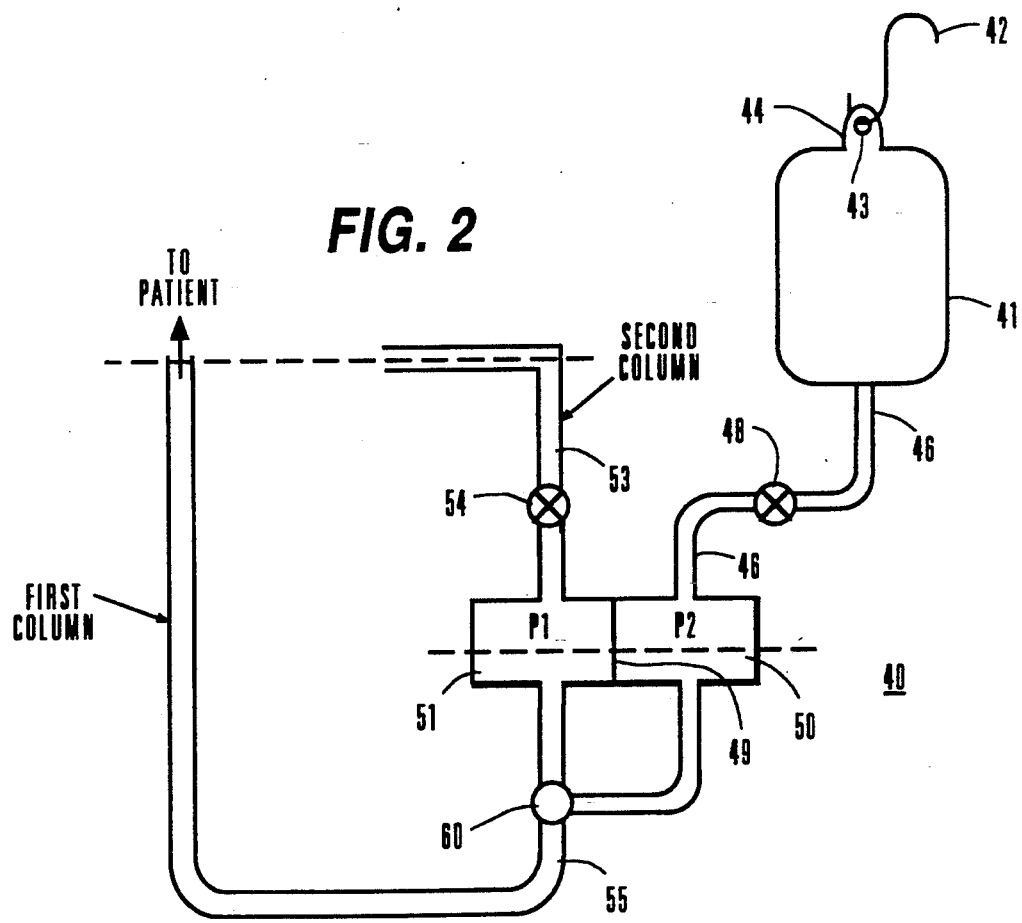
FIGS. 2, 3, and 4 are schematic illustrations of alternative patient fluid delivery systems in accordance with the principles of this invention.

FIG. 2 shows a pressure monitoring system in accordance with the principles of this invention. The system includes an additional tube communicating with the backside surface (22) of the sensor. The tube is filled partially with fluid and is maintained at atmospheric pressure. The fluid in the tube is operative to normalize any change in pressure in the system due to a change in the relative heights of the patient and the sensor.

Specifically, FIG., 2 shows a pressure monitoring system 40. The system includes a fluid container or bag 41 analogous to bag 11 of FIG. 1. The bag again is hung from a stand (not shown) by hook 42 engaging a hole 43 in extension 44 at the top of the bag.

A tube 46 exits the bag at the bottom, as viewed, and communicates, via a stop cock and restrictor assembly 48, with pressure sensor 49. Pressure sensor 49 separates two chambers 50 and 51. Tube 46 communicates with chamber 50. A second tube 53 communicates with chamber 51 via stop cock assembly 54. Chambers 50 and 51 are connected to a tube 55 via stop cock assembly 60. Importantly, tube 53 is partially filled with fluid and both surfaces of the sensor are exposed to fluid. In the embodiment of FIG. 2, tube 53 is open to air.

In normal operation, the system is first flushed by closing stop cock assembly 60 to the patient, thus interrupting the fluid path and opening the path from path 46 to path 53. Thus, stop cock assembly 60 is a three or four way stop cock connecting path 46 to path 55 to the patient, connecting paths 46 and 53 to one another, and closing off or opening all paths. The system next is changed by the adjustment of stop cock assembly 60 to connect path 46 to path 53 and closing off path 55. The system is now flushed out to remove air. Pressure P2 in path 46 is now isolated. It is to be understood that the P1 side (path 53) contains fluid and, in the embodiments of FIG. 2, that fluid is contained in a tube which is open to air.

Figure 3:
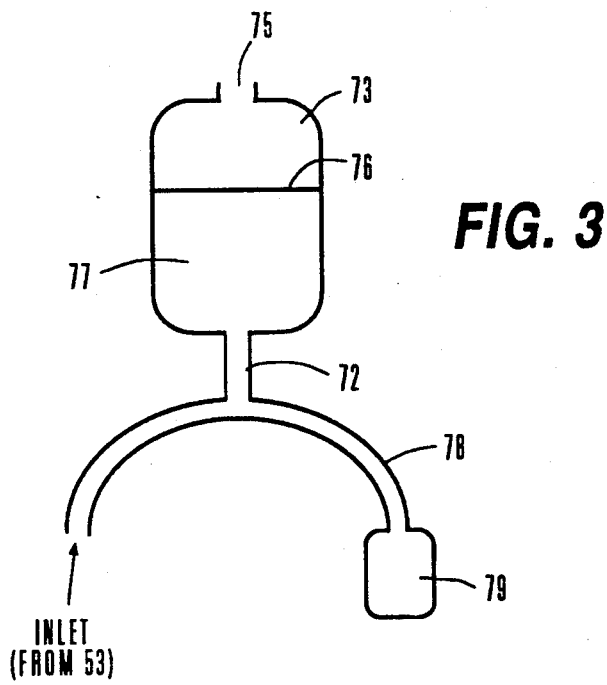

FIG. 3 shows an embodiment where the second column is not open to air, but is separated from air by a diaphragm which is permeable to air but not to the fluid contents of the path. Specifically, FIG. 3 shows a tube 72 which corresponds to tube 53 of FIG. 2. Tube 72 terminates at the top, as viewed, in a reservoir 73 which is open at 75. In this embodiment, a diaphragm or partition 76 separates the fluid contents, indicated at 77, from air. The diaphragm is aerophilic comprising illustratively Teflon which pass air but not the fluid contents.

A drain tube 78, having a diameter smaller than that of the inlet tube, as shown, terminates in a reservoir 79.

Figure 4:
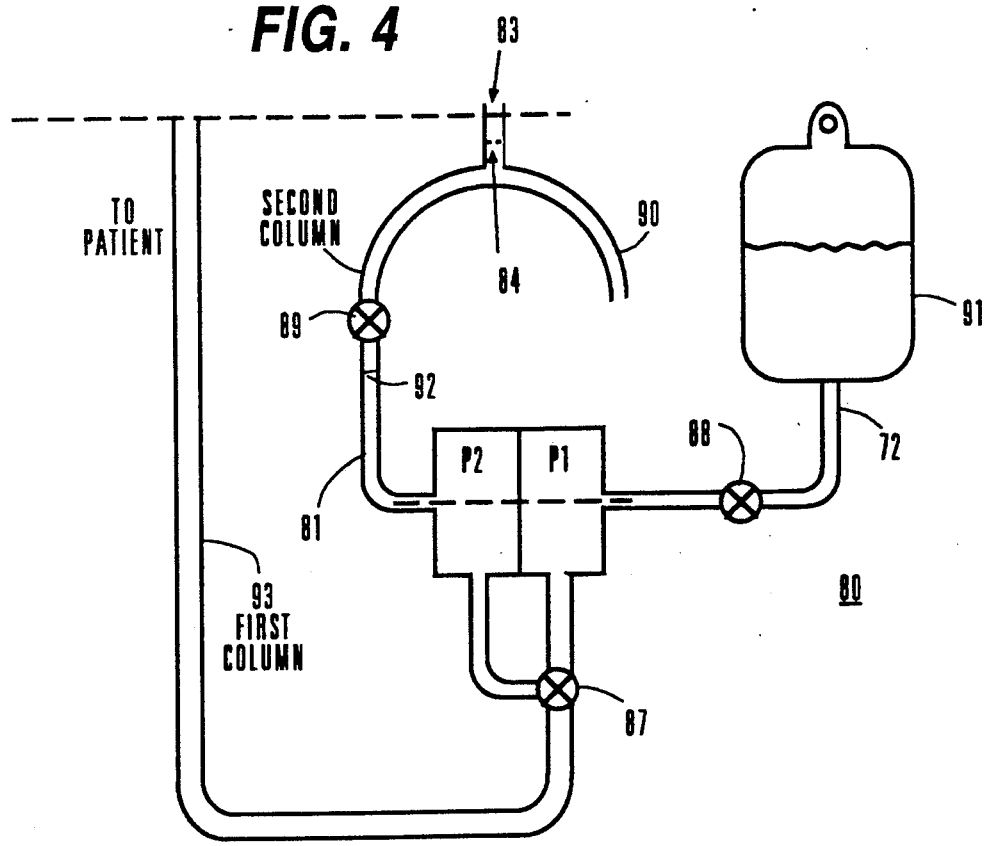

FIG. 4 shows an embodiment 80 corresponding to the embodiment of FIG. 2 where path 81 corresponds to path 53 of FIG. 2. In this embodiment, the tube defining path 53 is in the form of an upside down U with an opening to air at the "top" of the U as shown at 83, in one embodiment, or including a aerophilic diaphragm, shown dotted at 84, in a separate embodiment. FIG. 4 also shows a plurality of stop cocks 87, 88, and 89 corresponding to stop cocks 48, 54, and 60 of FIG. 2. Drain tube 90 terminates in an open bag not shown.

In all the embodiments herein, the proximal end of the pressure compensating tube (second column) may be attached to the chest wall of a patient, illustratively, by means of a suction cup nipple frequently used for EKG readings and by clamping the proximal end of the tube to the nipple. Any vertical movement of the patient relative to the fluid reservoir (viz: top of the second column in FIG. 4) results in a change in the height 92 of the fluid level in path 81. No change in the pressure in the fluid path 93 to the patient occurs. Thus, the main cause of change in blood pressure readings is avoided resulting in a significant reduction in the demand for attention by health care specialists, a concomitant reduction in associated costs and a safer response by such specialists.

The embodiments of FIGS. 2, 3, and 4 utilize a wet/wet sensor. Such a sensor is available from Motorola.

What is claimed is:

1. A pressure sensing system for monitoring pressure in a first column of fluid which is closed and under a pressure to be measured, said system including a pressure sensing device having first and second major surfaces, said first surface communicating at a first end with the fluid in said first column, said system including a second column of fluid, said second surface communicating with said second column, and means for maintaining the heights of said first and second columns equal to one another.

2. A pressure sensing system as set forth in claim 1 also including electronic display means, said sensing device being connected to said display means for providing an indication of the pressure of fluid in said first column.

3. A pressure sensing system as set forth in claim 2 wherein said first column is connected between said sensing device and a patient for measuring physiological pressures.

4. A pressure monitoring system for patient end use, said system comprising a first fluid column for delivering fluids to said patient, said fluid column being connected to a pressure sensor at a proximal end thereof and being adapted at a distal end thereof to mate with a needle for connection to said patient, said system including a second column, said second column also containing fluid and communicating with said first column, said second column also including means for maintaining atmospheric pressure therein for normalizing any pressure changes in said first column, said pressure sensor having first and second surfaces communicating with the fluid in said first and second columns respectively.

5. A pressure sensing system as set forth in claim 4, said system also including regulating means for controlling fluid flow in said first and second columns respectively, said system also including valve means for interrupting fluid flow to a patient and for permitting fluid communication from said first or second paths or from both of said first and second paths to said patient selectively.

6. A system as set forth in claim 5 wherein said second column is open to air at a first end.

7. A system as set forth in claim 5 wherein said second column includes a partition at a first end thereof, said partition being of a material to pass air but not said fluid.

8. A system as set forth in claim 7 wherein said partition comprises an aerophilic material.

9. A system for monitoring the pressure of fluid in a tube connected between a pressurized fluid source and a patient, said system comprising said fluid source, a tube connected to said fluid source at a proximal end thereof and to a needle at the distal end thereof for inter vascular connection to said patient, said tube including first valve means for interrupting fluid flow in said tube, said system also including a second tube, said second tube including a second valve means for interrupting fluid flow in said second tube, said second tube also including means at the distal end thereof for maintaining fluid in said second tube at atmospheric pressure and control means at the proximal end thereof for controllably interconnecting said second path to said first path, said system including pressure sensing means having first and second surfaces exposed to fluid in said first and second tubes respectively.

10. A system as set forth in claim 9 wherein said means for maintaining said second tube at atmospheric pressure comprises an opening to air in the distal end of said second tube.

11. A system as set forth in claim 10 wherein said means for maintaining said second tube at atmospheric pressure comprises a partition which passes air but not said fluid.

* * * * *